(12) United States Patent
Lowney et al.

(10) Patent No.: US 7,586,611 B2
(45) Date of Patent: Sep. 8, 2009

(54) METHOD AND APPARATUS FOR ANALYSIS OF SEMICONDUCTOR MATERIALS USING PHOTOACOUSTIC SPECTROSCOPY TECHNIQUES

(75) Inventors: Donnacha Lowney, Dublin (IE); Patrick McNally, Dublin (IE); Alec Reader, Mettet (BE)

(73) Assignee: Dublin City University, Dublin (IE)

( * ) Notice: Subject to any disclaimer, the term of this patent is extended or adjusted under 35 U.S.C. 154(b) by 207 days.

(21) Appl. No.: 10/557,950

(22) PCT Filed: May 21, 2004

(86) PCT No.: PCT/IE2004/000076

§ 371 (c)(1),
(2), (4) Date: Jan. 19, 2006

(87) PCT Pub. No.: WO2004/104562

PCT Pub. Date: Dec. 2, 2004

(65) Prior Publication Data

US 2006/0256339 A1  Nov. 16, 2006

(30) Foreign Application Priority Data

May 23, 2003  (IE) ................................ S2003/0396

(51) Int. Cl.
*G01N 21/00* (2006.01)
(52) U.S. Cl. .......................... 356/432; 356/473; 73/587; 73/24.02
(58) Field of Classification Search ................. 356/432, 356/273, 73, 326, 216, 217, 473; 250/492.1; 73/587, 24.02
See application file for complete search history.

(56) References Cited

U.S. PATENT DOCUMENTS 4,184,768 A    1/1980   Aamodl et al.

(Continued)

FOREIGN PATENT DOCUMENTS

EP    0 352 789 A    1/1990

(Continued)

OTHER PUBLICATIONS

Zakrzewski J et al: "Photoacoustic investigations of beryllium containing wide gap II-VI mixed crystals" Microelectronics Journal, *Mackintosh Publications LTD. LUTON, GB, vol. 31, No. 9-10, Oct. 2000, pp. 821-824, XP004218846 ISSN: 0026-2692 figure 1.

(Continued)

*Primary Examiner*—Gregory J Toatley, Jr.
*Assistant Examiner*—Abdullahi Nur
(74) *Attorney, Agent, or Firm*—Tarolli, Sundheim, Covell & Tummino LLP

(57) ABSTRACT

A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising a light source having a polychromatic output substantially in the photonic energy range 0.5 eV to 6.2 eV, focusing means adapted to couple the output from the light source onto the sample material, the focusing means providing for an alignment and focusing of the light emitted from the light source so as to provide a substantially parallel incident light onto the sample material, and means for detecting and acquiring the acoustic signal emitted by the sample in response to the irradiation. A method of providing an acoustic signal spectrum emitted by a sample material provided within a photoacoustic cell following irradiation of the sample by an incident light beam is also provided.

60 Claims, 7 Drawing Sheets

U.S. PATENT DOCUMENTS

| | | | |
|---|---|---|---|
| 4,436,428 A * | 3/1984 | Watanabe et al. | 356/432 |
| 4,448,525 A | 5/1984 | Mikoshiba et al. | |
| 5,537,336 A * | 7/1996 | Joyce | 702/108 |
| 5,933,245 A * | 8/1999 | Wood et al. | 356/437 |
| 2003/0043880 A1 * | 3/2003 | Meyler et al. | 374/32 |

FOREIGN PATENT DOCUMENTS

| | | |
|---|---|---|
| JP | 59 061750 A | 4/1984 |
| JP | 05 107232 A | 8/1993 |

OTHER PUBLICATIONS

Ohmukai M et al: "Two kinds of enhancement in photoluminescence by chemical etching of porous silicon" Materials Science and *Engineering B, Elsevier Sequota, Lausanne, CH, vol. 95, No. 3, Sep. 1, 2002, pp. 287-289, XP004377871 ISSN: 0921-5107 figure 1.

Bribiesca S et al: "Photoacoustic thermal characterization of electrical porcelains: effect of alumina additions on thermal diffusivity *and elastic constants" Journal of the European Ceramic Society, Elsevier Science Publishers, Barking, Essex, GB, vol. 19, No. 11, *Sep. 1999, pp. 1979-1985, XP004171885 ISSN: 0955-2219 figure 1.

Yoshino K et al: "Photoacoustic spectra of zincselenide thin films grown by molecular beam epitaxy" Microelectronic Engineering, Elsevier *Publishers BV., Amsterdam, NL, vol. 43-44, Aug. 1, 1998, pp. 689-693, XP004148242 ISSN: 0167-9317 figure 1.

* cited by examiner

METHOD AND APPARATUS FOR ANALYSIS OF SEMICONDUCTOR MATERIALS USING PHOTOACOUSTIC SPECTROSCOPY TECHNIQUES

FIELD OF THE INVENTION

The invention relates to Photoacoustic Spectroscopy (PAS), and in particular to techniques and apparatus using photoacoustic spectroscopy in the analysis of semiconductor materials. Such materials may include direct or indirect bandgap semiconductors having bandgaps in the range of about 0.5 eV$<E_G<$6.2 eV. Examples of such semiconductors include infrared detector materials (eg. InAs), and wide bandgap semiconductors for blue/violet/UV light emissions and high temperature electronics (e.g. GaN, SiC or diamond). Further examples include Si and GaAs.

Photoacoustic spectroscopy techniques can be divided into direct and indirect methodologies. In direct photoacoustic spectroscopy, a photoacoustically generated wave is produced in a sample where an excitation beam is absorbed. The photoacoustically generated wave is typically measured by a piezoelectric transducer bonded to the sample. The invention is, however, more particularly directed to indirect techniques. In indirect photoacoustic spectroscopy, an acoustic wave is generated in a coupling medium adjacent to a sample to be analysed, e.g. via a "thermal piston" effect, resulting in a heating of an air column directly above the excited region of the sample. The heating of the air column results in measurable pressure fluctuations.

The inherent advantage of indirect photoacoustic spectroscopy for the investigation of, for example, stress and defect related phenomena in semiconductor materials is that it is non-invasive compared with direct photoacoustic spectroscopy.

BACKGROUND TO THE INVENTION

Advances in the microelectronics industry have been underpinned by improvements in the quality of the constituent device materials. Consider for example silicon: in the 1970s the dislocation density was of the order of $10^3$ cm$^{-2}$, whereas today defect free wafers with a diameter of up to and greater than 400 mm are being used in the production of microprocessors. The characterisation and understanding of defects within semiconductor materials is necessary if device performance is to be enhanced. The structural and opto-electronic properties of a material are interrelated and thus neither can be examined in isolation of the other. Of particular importance is the influence of structural defects on the opto-electronic properties of the material, as these are known to affect carrier diffusion lengths, radiative and non-radiative recombination processes.

Photoacoustic spectroscopy (PAS) is a non-invasive photocalorimetric technique that can probe the non-radiative thermal de-excitation channels of a sample and hence compliments absorption and other spectroscopic analysis methods. Only light absorbed within the sample can generate a photoacoustic response and thus, elastic scattering or transmission of light through the sample does not influence this highly sensitive technique. Photoacoustic spectroscopy can be used to measure amongst others, the absorption spectrum, lifetime of photo-excited species and thermal properties of a sample.

The photoacoustic effect was first reported in 1880 by Alexander Graham Bell in a report to the American Association for the Advancement of Science. After the work of Bell, the photoacoustic effect was largely ignored until the latter half of the 20$^{th}$ century because the technical equipment, such as phase sensitive amplifiers and microphones, necessary to obtain accurate results did not exist. The first theoretical description of the photoacoustic effect in non-gaseous samples was made in the early 1970's and several classical extensions were made to this theory before the first semiclassical description of the photoacoustic effect in semiconductors was published in the early 1980's. Essentially, these theories describe how light absorbed in a sample following non-radiative de-excitation processes gives rise to a heat source in the sample that may be distributed throughout the sample volume or confined to its surface. This heat source generates both temperature and pressure fluctuations within the sample, which in turn induce measurable pressure variations within the gas in contact with the sample.

The basic mechanism behind photoacoustic spectroscopy is as follows. Intensity modulated monochromatic light is shone on a sample. Non-radiative de-excitation processes following light absorption consequently heat the sample. By convective processes, the sample in turn heats up a gas layer in the immediate vicinity of the point of light absorption. The modulated nature of the light induces corresponding pressure fluctuations in the gas due to repetitive heating and cooling of the sample. These pressure fluctuations are detected in the case of indirect photoacoustic spectroscopy by a microphone and are known as the photoacoustic signal. A photoacoustic spectrum may be obtained by determining the photoacoustic signal of the sample as a function of the wavelength and modulation frequency of the incident light.

The Extension of PAS to Semiconductors

It will be appreciated that electron excitations, having a finite lifetime, are generated in the process of light absorption. This absorption of light is accompanied by the generation of electron-hole pairs, which exist for a finite lifetime and move within the sample, before transferring their energy back to the sample in the form of heat.

It is known that a photoacoustic spectrum can be used in an evaluation of the optical absorption coefficient and the bandgap energy of a semiconductor sample. The first theory of the photoacoustic effect in semiconductors was developed in the 1980s by Bandeira et al. Several groups tried to improve their theory, but all quintessentially possessed the same foundations. In their study, Bandeira and co-workers were interested in enhancing the photoacoustic effect from samples with low optical absorption coefficients. To this end, they applied an electric field across the sample perpendicular to the direction the incident photons made with the sample. The subsequent Joule heating enhanced the contribution to the photoacoustic signal from photoexcited carriers in the bulk. The application of this technique was limited to an analysis, non-destructively, of the bandgap of semiconductors, direct or indirect.

This technique is also capable of analysing non-destructively:

1. The energy location of sub-bandgap defect levels, which are the prime cause of non-radiative recombination, and thus are detrimental to optoelectronic device operation.
2. The impact of dislocation generation in strained layer epitaxial systems for modem electronic and opto-electronics materials and devices. In un-strained, defect-free substrate material, one only observes an increase in the photoacoustic signal during the bandgap transition. As an epitaxial layer is grown on the substrate, any induced strain will modify the band-structure, possibly providing alternative non-radiative recombination paths for photoexcited carriers. The presence of such levels would be seen as peaks in the spectrum below the bandgap energy. The energy levels of these defects can be inferred directly from the PAS spectrum.
3. The optical absorption coefficient (β) of the semiconductor, for direct or indirect bandgap materials. Through a knowledge of the normalised photoacoustic spectrum and the thermal diffusion length of the sample, it is possible to determine the optical absorption coefficient of the sample.
4. Elastic and thermoelastic properties of the material under investigation.

Photoacoustic spectrometers for the analysis of gaseous substances are commercially available. However, photoacoustic spectrometers for condensed matter analysis are difficult to obtain and are often unsuitable in their construction to the varied needs of a semiconductor experimentalist. This has been the impetus for the development of in-house systems, which are typically designed for specific experimental conditions and a narrow range of type of materials. The design process for many of these systems has been quite arduous, expensive and very involved.

Photoacoustic spectrometry requires the use of an intensity modulated monochromatic light source to induce the photoacoustic effect in the semiconductor. For this purpose, pulsed and continuous lasers are popular. Due to the inherent wavelength properties of such lasing devices, it will be appreciated that they are only useful over a narrow photonic range, the range of operation of the laser. Zegadi et al. (*Rev. Sci. Instrum.* 65 (7), July 1994) discuss the use of a non-laser device. They disclose the use of a short arc xenon lamp as a light source in the examination of spectra in the near infrared portion. Although this light source has specific application in the region of interest described in Zegadi, it suffers in that the resolution of the incident light on the sample is not as good as what is achievable using lasers. They nevertheless discuss how they believe the resolution of their apparatus is a high resolution arrangement. It will be appreciated from a review of their disclosure that this reference to high resolution is a reference to for example "high energy resolution" as would be found in a typical energy vs. PA Signal plot.

There is, therefore, a need to provide a photoacoustic system that has an extended wavelength range such that it can be used in the analysis of a wide variety of semiconductor sample types, yet maintains an incident light source of sufficient spatial resolution so as to spatially distinguish the location of any defects detected on the sample.

It is therefore an object of the present invention to provide a spectrometer having a light source whose emission spectra is suitable to effect a radiation of samples of differing semiconductor constituency yet maintains resolution so as to enable a spatial discrimination of the location of detected defects in a sample.

Extension of PAS to Measurement of Dielectric Anisotropy

Dielectric thin films are used in numerous applications in semiconductor device fabrication, e.g. pad oxides, inter-level dielectrics, etc. As device dimensions shrink, a precise knowledge and control is required of the nature of the dielectric constant. Dielectric anisotropy is a state in which the dielectric constant parallel to the one axis is different from the dielectric constant perpendicular to that axis.

To date, measurement of these anisotropies requires a direct measurement of capacitance structures on the material under test. The results are both specific only to that capacitance structure and are obtained invasively.

It is an object of the present invention to provide a method and apparatus for the non-destructive and non-invasive measurement of dielectric anisotropies.

SUMMARY OF THE INVENTION

Accordingly the present invention provides a photoacoustic spectrometer for use in the photonic energy range 0.5 eV to 6.2 eV for the observation and characterisation of non-radiative sub bandgap defects in narrow and large bandgap materials.

In a preferred embodiment, a photoacoustic spectrometer is provided having a high power short arc lamp with a high resolution monochromator, wherein the characteristics of the beam which is incident on the sample is alterable by the provision of an optical system at the output of the monochromator to vary the spatial resolution of the incident beam.

Desirably, the present invention provides a system which, at a reasonable cost, acquires relative information about a sample of semiconductor material by normalising the spectra, obtained using photoacoustic spectroscopy techniques, to that of a known sample (e.g. carbon black powder).

In preferred embodiments, a high power short arc lamp is used and it will be appreciated that such a lamp is more economical than a laser. However, it will be further appreciated that in alternative embodiments, a photoacoustic spectrometer may be provided having a laser system with an Optical Parametric Amplifier (OPA), or an Optical Parametric Oscillator (OPO).

In a first embodiment, a photoacoustic spectrometer apparatus is provided which is adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:
  a light source having a polychromatic output substantially in the photonic energy range 0.5 eV to 6.2 eV,
  focusing means adapted to couple the output from the light source onto the sample material, the focusing means providing for an alignment and focusing of the light emitted from the light source so as to provide a substantially parallel incident light onto the sample material, and
  means for detecting and acquiring said acoustic signal emitted by the sample in response to said irradiation.

The apparatus typically includes means for modulating the polychromatic light, such as a modulator. The means for modulating typically includes an optical chopper.

The apparatus desirably additionally includes a monochromator provided between the light source and the focusing means, the monochromator adapted to convert the modulated polychromatic light into modulated monochromatic light.

The monochromator may comprise means for altering the output slit width to optimise one or more of incident power, spectral and spatial resolution, PA signal-to-noise rations, etc. The altering means may be computer controlled.

Means may further be provided to vary the input slit to the monochromator for one or more of the aforementioned reasons. The means for varying the slit may be manually controlled or computer controlled. An advantage with computer control is that a constant bandpass may be provided over the energy range of interest.

The means for detecting said acoustic signal desirably includes a plurality of microphones provided within the photoacoustic cell, the microphones being adapted to detect an acoustic emission from the sample upon radiation by the light source and couple that signal to the means for acquiring said signal. The microphones are typically of the type known as electret microphones. It will be appreciated that any suitable detector may be used as the means for detecting the acoustic signal.

Preferably, the means for detecting and acquiring said acoustic signal emitted by the sample detects and acquires a signal associated with a sub-range defined within the photonic energy range output of the light source.

The means for detecting and acquiring said acoustic signal desirably includes data acquisition and processing means and signal processing means. The data acquisition and processing means may be a data processor and the signal processing means a signal processor. In one embodiment of the invention, numerous spectra may be recorded. Data obtained by this means may be numerically processed through for example, averaging or filtering processes or algorithms. The means for detecting said signal desirably includes:

- means for pre-amplifying an electrical signal, such as a low-noise pre-amplifier, and
- means for detecting signal, such as a lock-in amplifier.

In one embodiment of the invention, a signal from the microphone is passed through a low-noise pre-amplifier to a lock-in amplifier. The amplified signal may then be passed to a computer.

It will be appreciated that in some embodiments of the invention, a plurality of microphones may be provided. The respective signals from the plurality of microphones may be added and sent as a single signal to a lock-in amplifier. It will be appreciated that additional circuitry may be provided to maximise the signal. This would have the effect of preventing the generation of a weak lock-in signal due to signals out of phase quadrature combining.

The photoacoustic cell may be provided with an inert atmosphere such as helium gas. The use of such gases which have associated high thermal conductivity will absorb more heat from the sample than for example air.

The apparatus may additionally include means for cooling the cell to below 273K.

The means for cooling, or cooler, may be adapted to maintain the cell at temperatures in a controllable range from about 77K to about room temperature by means of apparatus such as a cryostat (for temperatures down to 77K) or Peltier cooler (for 215K-273K range). It will be appreciated that alternative arrangements may be provided for cooling the cell. It will further be appreciated that in accordance with the classical photoacoustic theory of Rosencwaig and Gersho that this cooling will serve to improve the photoacoustic signal-to-noise ratio.

The apparatus may include means for heating the cell.

In one embodiment, such heating means may comprise means for applying an electric field across the sample material in a direction perpendicular to the direction of the incident light, to encourage Joule heating of the sample.

Preferably, the apparatus comprises means for recording the acoustic signal over a range of temperatures, so as to enable the relationship between temperature and the acoustic signal to be investigated.

The focusing means are desirably adapted to provide an incident light of not greater than about 15 mm in diameter, the diameter of the incident light being substantially equivalent to the spatial resolution achievable.

The focusing means, or focusing apparatus, desirably includes a first and second optical focusing system: the 1st optical focusing system adapted to provide for a maximisation of the photonic throughput thereby maximising the intensity of light incident on the sample (and hence the photoacoustic signal as it is directly proportional to the intensity of the incident light), and the 2nd optical focusing system being adapted to provide for an increment in the spatial resolution of the light.

The first optical system is desirably adapted to provide for a magnification factor of the image of less than 1 and preferably about 0.3. To effect such a magnification factor, the first optical system typically utilises a two lens arrangement, the magnification of the system being a combination of the combined magnification of the individual lenses. The first lens is desirably configured to provide a virtual image as the source image which then provides a real image as the incident light on the sample. A variance of the distance between the two lens may be effected to vary the size of the beam incident onto the sample. Typically, the first and second lenses are provided by a biconcave and biconvex lens respectively.

The 2nd optical focusing signal is adapted to provide for spatial mapping of the photoacoustic signal produced at the cell. Spatial resolution of the beam may be provided by a tight focusing of the incident light (to ~1 mm spot size, yielding best resolutions also of ~1 mm). Means may be provided to allow relative movement between the beam and the sample to enable different portions of the sample to be analysed. Desirably, the photoacoustic cell is mountable on a computer controlled X-Y translational stage so as to enable a movement of the cell relative to the incident light. Such relative movement enables the formation of a spatially resolved map (for example ~1 mm lateral spatial resolutions) of the PA signal to be computed.

The second optical system desirably comprises a plurality of optical components which are adapted to re-configure the spatial dimensions of the light emitted from the monochromator so as to form an incident light beam which, in a preferred embodiment, is substantially circular in cross-section. It will be appreciated however that alternative geometrically shaped beams may be provided.

Typically, the second optical system includes:

- a cylindrical lens adapted to re-configure the dimensions of the light incident thereon, the cylindrical lens providing a light beam substantially circular in cross section as an output thereof,
- a concave mirror adapted to re-direct and focus the substantially circular light onto a 1st plane mirror which is adapted to further re-direct the light beam so as to provide a source image for the first optical system, and
- a 2nd plane mirror adapted to receive the magnified output from the first optical system and re-direct that light onto the sample within the photoacoustic cell.

The combination of the lens and mirror assembly provided by the first and second systems desirably delivers a circular shaped beam incident on the sample with a diameter variable between 1 mm and 12 mm.

The combination of a cylindrical lens, which it will be appreciated effects a focusing in one plane only, and a concave mirror, which focuses in both planes, generates an image on the 1st plane mirror substantially equal in size in both horizontal and vertical directions, The apparatus is desirably adapted to provide for a fully automated spatial resolved photoacoustic scan of a sample material. This provides for an analysis of the results of the scan during or shortly after the scan (i.e. in real time) and then a subsequent repositioning of the beam on areas of interest to obtain further results in such regions.

Desirably, the apparatus comprises means for varying the chopping frequency of the incident beam. Varying the chopping frequency enables the photoaccoustic probe depth (the penetration depth of the beam) in the sample to be controlled.

It will be appreciated that such depth controlling enables depth profiling of the sample to be investigated. The means for varying the chopping frequency may include the computer in conjunction with the lock-in amplifier.

According to one aspect of the invention, the apparatus may further comprise a polarising filter located between the focusing apparatus and the photoacoustic cell. The polarising filter is adapted to polarise the incident light beam. Thus the light incident on the sample is polarised. Using the addition of a polarising filter allows the photoacoustic response to be recorded as a function of polarisation.

Preferably, the polarising filter comprises an adjustor for adjusting the direction of the polarisation of the incident light beam.

Desirably, the adjustor is adapted to rotate the polarising filter in a plane perpendicular to the direction of the incident light beam. The adjustor may be a rotatable stage on which the polarisation filter is mounted.

The adjustor for rotating the polarising filter may be automatically controlled. Desirably the adjustor is motorised.

Using a motorised rotational stage, it is possible to incrementally change the polarisation then record the photoacoustic signal. By recording the photoacoustic response as a function of polarisation, it is possible to measure dielectric anisotropies within a sample of dielectric material.

The present invention further provides a method of providing an acoustic signal spectrum emitted by a sample material provided within a photoacoustic cell following irradiation of the sample by an incident light beam, the method comprising the steps of:
a) providing a light source having a polychromatic output substantially in the photonic energy range 0.5 eV to 6.2 eV,
b) setting the wavelength of the light source to an initial first irradiating wavelength,
c) irradiating the sample with said light source and detecting the acoustic signal emitted by the sample at said wavelength,
d) incrementing the wavelength by a sequence of increment values so as to provide a plurality of irradiating wavelengths and detecting the acoustic signal emitted by the sample at each of said irradiating wavelengths, and relating each of the detected acoustic signals to the incident wavelength effecting generation of said acoustic signal.

Desirably, the sample material is selected from groups within the periodic table having one or more of the following:
a) infrared detector materials (e.g. InAs),
b) wide bandgap semiconductors for blue/violet/UV light emissions,
c) high temperature electronics (e.g. GaN, SiC or diamond), and
d) Si or GaAs based materials.

It will be appreciated that the apparatus of the present invention is not limited to use in the methods described herein. It is therefore possible that the apparatus may be adapted for use in alternative experimental procedures. For example, the temperature of the sample or the temperature of the gas in the cell may be varied. By examining a particular defect level as a function of sample temperature it may be possible to obtain direct information on phonon mediated or non-radiative processes. In one embodiment, liquid helium may be use to cool the sample held in the cell, at which temperature the non-radiative or phonon mediated effects should disappear or be significantly reduced.

Another such use is in the study and measurement of dielectric anisotropies. The invention further provides a method of providing an acoustic signal spectrum emitted by a sample material provided within a photoacoustic cell following irradiation of the sample by an incident light beam, the method comprising the steps of:
a) providing a light source having a polychromatic output substantially in the photonic energy range 0.5 eV to 6.2 eV,
b) polarising the incident light beam from the light source,
c) irradiating the sample with said polarised light beam and detecting the acoustic signal emitted by the sample,
d) adjusting the direction of polarisation so as to provide polarisation in a plurality of directions and detecting the acoustic signal emitted by the sample at each direction of polarisation, and relating each of the detected acoustic signals to the polarization direction of the incident light effecting generation of said acoustic signal.

Desirably, the step of polarising the incident light beam comprises the step of positioning a polarising filter in the path of the incident light beam.

Preferably, the step of adjusting the direction of polarisation comprises the step of rotating the polarising filter in a plane perpendicular to the direction of the incident light beam.

These and other features of the present invention will be better understood with reference to the following drawings.

DETAILED DESCRIPTION OF THE DRAWINGS

Figure 1:
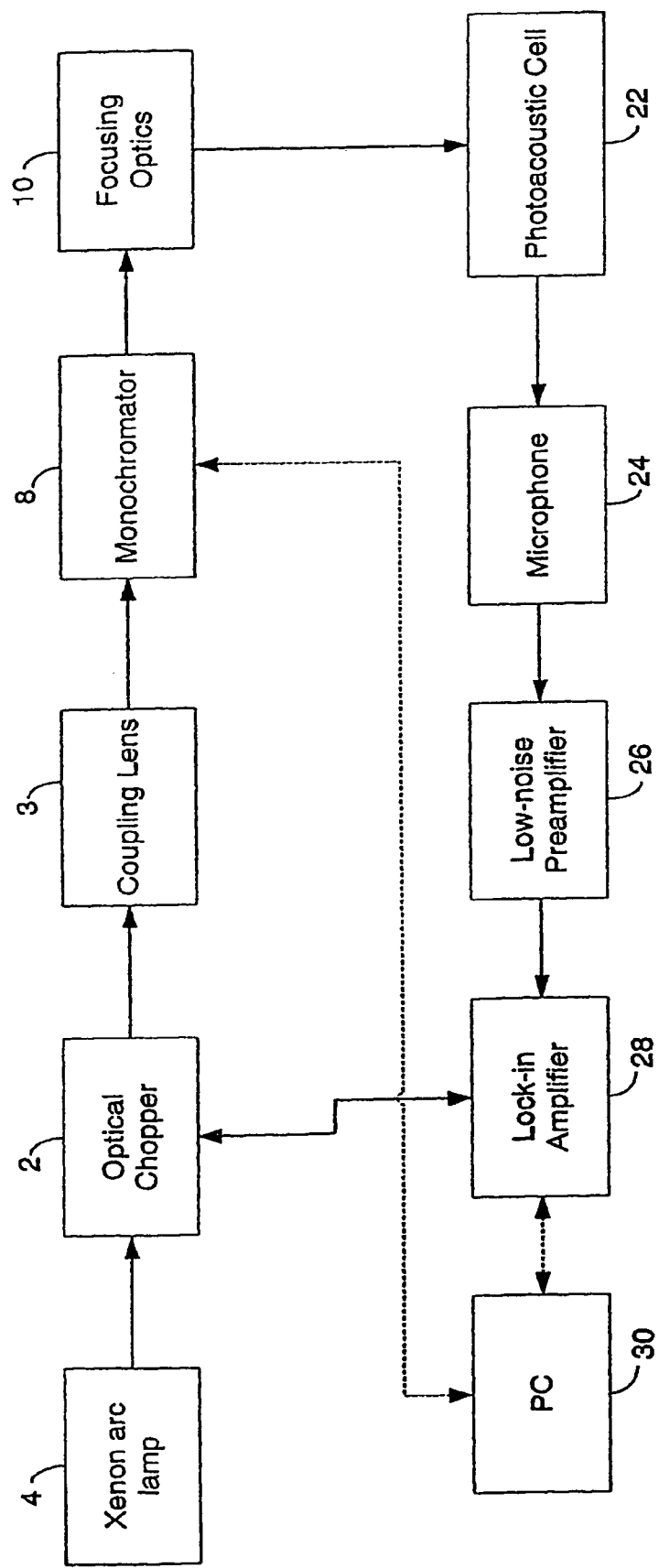
FIG. 1 is a schematic representation of a photoacoustic spectrometer according to a first aspect of the present invention.

FIG. 1 is a schematic representation of a photoacoustic spectrometer according to one embodiment of the present invention.

In use, an optical chopper 2 modulates polychromatic light from a 300 W Xenon arc lamp 4 as it is focused, using a coupling lens 3, onto an entrance slit of a monochromator 8. The amplitude-modulated light that enters the monochromator 8 undergoes diffraction in accordance with the grating equation:

$$g\lambda = a \sin \theta \quad (1)$$

where g is the order of the reflection, $\lambda$ the monochromatic diffracted wavelength, a the line spacing of the grating and $\theta$ the diffraction angle. The order sorting filter wheel at the output of the monochromator ensures that only light with wavelength λ is transmitted and the harmonic contribution from wavelengths λ/g where g≧2 are rejected.

At this stage the monochromatic light enters a dual configuration focusing system 10, from which it is reflected into a photoacoustic cell 22 which, in use, contains a sample 20 of material to be analysed. The modulated monochromatic light is shone on the sample. Non-radiative de-excitation processes following light absorption consequently heat the sample. By convective processes, the sample in turn heats up a gas layer in the immediate vicinity of the point of light absorption. The modulated nature of the light induces corresponding pressure fluctuations in the gas due to repetitive heating and cooling of the sample. These pressure fluctuations are detected by a microphone 24 and are known as the photoacoustic signal.

The resulting electrical or photoacoustic signal is first pre-amplified in a low-noise pre-amplifier 26 before detection of the signal is performed with a lock-in amplifier 28. An internal frequency generator in the lock-in amplifier 28 provides the reference frequency for the optical chopper 4.

A photoacoustic spectrum may be obtained by determining the photoacoustic signal of the sample as a function of the wavelength and modulation frequency of the incident light.

The photoacoustic cell is mounted on a computer controlled X-Y translational stage. Thus, fully automated spatial resolved photoacoustic scans are possible. Using paraxial ray theory analysis, general component specifications are derived. Ray tracing analysis is used to determine the size of the beam striking the mirror as a function of the inter-lens distance.

The entire system is controlled by a personal computer 30 using software such as Lab View® software and the National Instruments IEEE 488.2 GPIB interfacing protocol.

Focusing System

Figure 2:
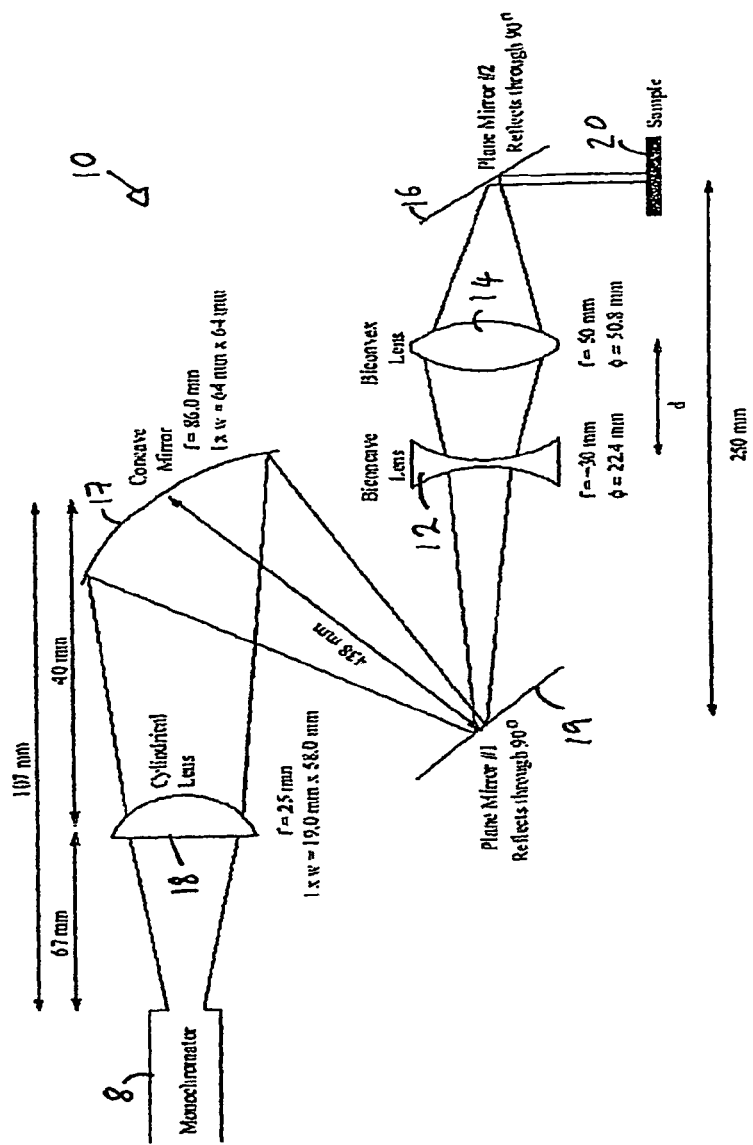
FIG. 2 is a schematic representation of the focusing system used in the photoacoustic spectrometer of FIG. 1.

The dual configuration focusing system 10 in the Photoacoustic Spectrometer of FIG. 1 is shown in detail in FIG. 2. It will be understood that the optics of the present invention are adapted to provide for intensity, maximisation and spatially resolved photoacoustic studies. In this section, the operation of the focusing optics will be explained. The only major design constraint is that the materials used in the lenses have to be as optically transparent as possible over the wavelength range of interest i.e. 200 nm to 2.4 μm and also that the entrance window to the cell must be substantially transparent over these ranges.

The focusing system of FIG. 2 comprises two subsystems. According to the present invention the focusing system is adapted to include optics which provide for:

(a) intensity maximisation, and (b) spatially resolved photoacoustic studies.

The first focusing subsystem is designed to maximize photonic throughput and thereby the intensity of light incident on the sample 20. A shown in FIG. 2, the first subsystem comprises a biconcave lens 12 and a biconvex lens 14 separated by a distance d.

In photoacoustic spectroscopy, the photoacoustic effect is directly proportional to the intensity of the incident light source $I_0$. This implies that as much of the power from the output port of the monochromator 8 should be focused into as small an area as possible. It will be appreciated that there is a lower limit to the area of the focused beam. If this area is too small, insufficient heating of the gas in contact with the sample within the cell may occur, thus failing to generate an appreciable pressure variation that can be measured by the microphone in the gas cell. Conversely, if the beam size is too big and hence the intensity of the incident light source $I_0$ is too low, then an insufficient signal may be generated. Using the example of the lens arrangement in the first focusing subsystem of FIG. 2 as providing a magnification factor of approximately m=0.3, it will be understood that for example, a 3 mm by 12 mm output beam from the monochromator 8 will be converted into a beam approximately 1 mm by 4 mm in size.

Starting with the basic lens equation:

$$\frac{1}{f} = \frac{1}{u} + \frac{1}{v} \qquad (2)$$

and reformulating the magnification of a single lens yields:

$$m_{sl} = \frac{v}{u} = \frac{f_{sl}}{u_{sl} + v_{sl}} \qquad (3)$$

where u is the object distance, v is the image distance and the subscript sl denotes single lens. This equation implies that for a real image to be formed by a single lens, two constraints must be satisfied:

1. The focal length, $f_{sl}>0$.
2. The object distance $u_{sl}>f_{sl}$.

If either of these constraints are ignored a virtual image will be generated. The second constraint implies $u_{sl}=af_{sl}$ for some a>1. Consequently, equation (3) may be re-written as:

$$m_{sl} = \frac{1}{\alpha - 1} \qquad (4)$$

Figure 3:
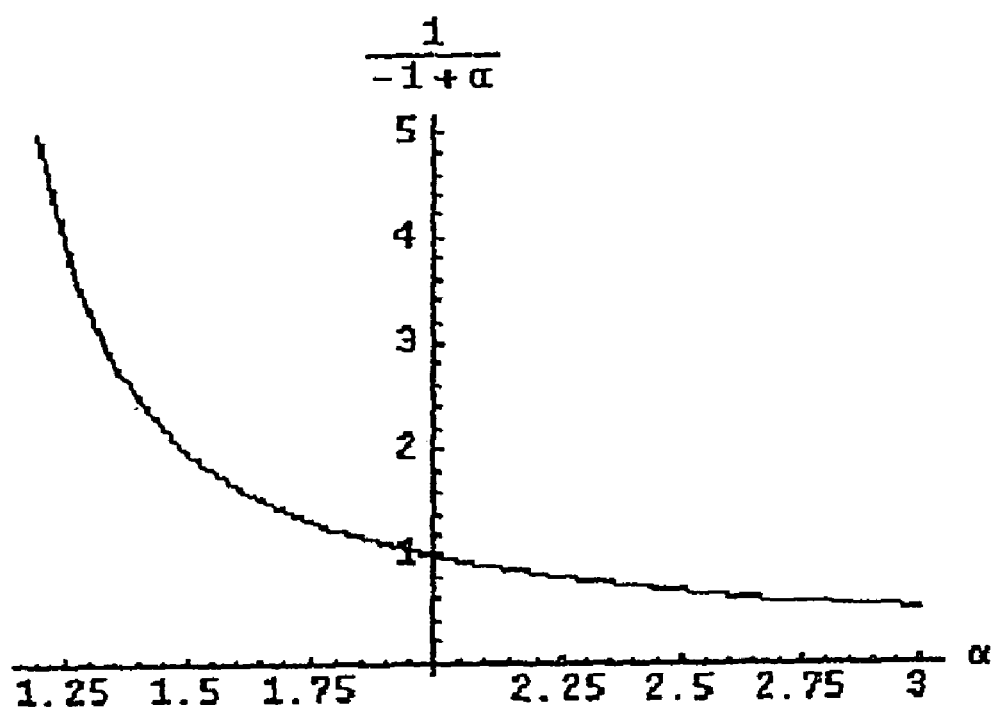
FIG. 3 is a plot of fractional variation in object distance versus magnification for a single lens.

FIG. 3 is a plot of fractional variation in object distance versus magnification for a single lens. The plot demonstrates that a single lens only provides realistic real image focusing in the magnification range 1≦m≦2. Outside this range the object distance becomes physically impractical with respect to the numerical aperture of the lens. Therefore, a two lens imaging system is used in the focusing system of the invention.

Figure 4:
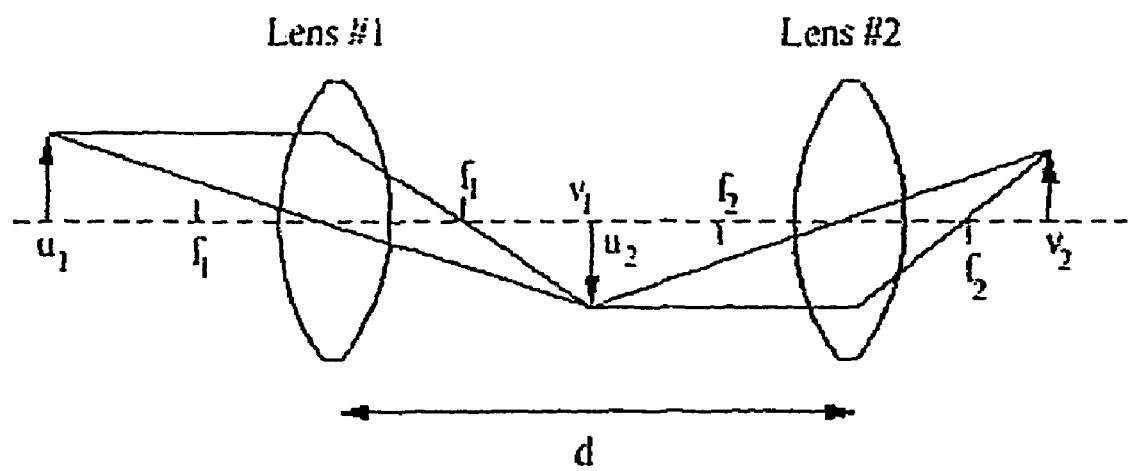
FIG. 4 shows an optical system consisting of two lenses separated by a distance d, used in Configuration (a) for maximal intensity throughput for the PAS system.

FIG. 4 shows an optical system consisting of two lenses separated by a distance d. Biconvex lenses have been drawn, however the mathematical derivation in the text applies to lenses with both positive and negative focal lengths once the sign convention is adhered to.

The object distances have been chosen to be greater than the focal lengths of the lenses to ensure real images are created. The magnification of the system is the combined magnification of the individual lenses:

$$m_{1,2} = m_1 m_2 = \frac{v_1}{u_1}\frac{v_2}{u_2} \qquad (5)$$

Since $$m_1 \frac{f_1}{u_1 - f_1} \qquad (6)$$

and $u_2=d-v_1$.

$$\Rightarrow m_{1,2} = \frac{f_1 v_2}{d(u_1 - f_1) - u_1 f_1} \tag{7}$$

Referring to the first focusing sub-system of FIG. 2 for use in the photoacoustic spectrometer of FIG. 1, it will be understood that in order to ensure a maximal throughput of intensity from the short-arc Xe lamp in the PAS system, the biconcave lens 12 has a focal length $f_1 = -30$ mm and the biconvex lens 14 has a focal length $f_2 = 50$ mm. In use, this configuration provides a combined magnification $m_{1,2} = -0.32$ for an inter-lens separation distance of 50 mm. The minus sign in the magnification means the image of the source is inverted. This is inconsequential as we assume equal irradiance in all parts of the beam, i.e. the beam is the same above and below the principal axis.

This lens configuration, which is seen implemented in FIG. 2, assures irradiance of the sample under test over regions of up to 15 mm in diameter, thus allowing for large signal-to-noise ratios in the photoacoustic signals, and consequently for rapid analysis times over the uniquely large energy excitation range of 0.5 eV through to 6.2 eV.

By varying the distance between the biconcave lens 12 and the biconvex lens 14 one can vary the size of the beam that strikes the second plane mirror. Therefore, in use, it is possible to vary the size of the beam which is reflected onto the sample using the second plane mirror 16.

The lens used in the system of FIG. 2 are desirably as optically transparent as possible over the wavelength range of interest, i.e. 200 nm to 2.4 μm.

The second focusing assembly of the photoacoustic spectrometer of FIG. 1 is designed for spatial mapping of the photoacoustic signal within the sample. As shown in FIG. 2, the second subsystem comprises a concave mirror 17, a cylindrical lens 18, a first plane mirror 19 and a second plane mirror 16.

The combination of the concave mirror 17 and cylindrical lens 18 (which focuses in one plane only) generates an image on the first plane mirror 19 that is the same size in the horizontal and vertical directions.

The output optical configuration for spatially resolved photoacoustic studies is now described. As shown in FIG. 2, the second sub-system focuses a 3 mm by 12 mm rectangular beam at the output port of the monochromator 8 into a circular shaped beam incident on the sample with a diameter variable between 1 mm and 12 mm. This design has been formulated in an iterative manner; we will therefore only describe the optimal solution.

Photoacoustic Gas Cell

In order to efficiently detect any photoacoustic signal emitted from an excited sample it is important that the photoacoustic cell within which the sample is placed meets a number of requirements. These requirements will be well known to those skilled in the art, and typically require a confined volume of gas whose volume is definable. An upper transparent window is provided through which the incident light can pass and impinge on the sample contained within the cell. One or more microphones are desirably provided within the cell to detect the acoustic signal emitted by the sample upon excitation.

Typically, the internal diameter of the active volume of such a cell is 30 mm and the gas column length is 5 mm, the cell having a fixed gas volume of 3.5 cm³. It will be appreciated however that these values are exemplary only and it is not intended to limit the dimensions of the cell of the present invention to any one set of values. Air at atmospheric temperature and pressure is typically used as the gas in the cell. However, other gases, e.g. Ar or He can be introduced instead of air. As the PA signal is proportional to the thermal conductivity of the gas in contact with the sample, it will be appreciated that by replacing the air in the cell with a gas having a different thermal conductivity to that of air, the photo acoustic signal generated within the cell may be enhanced. For example, helium could increase the signal by a factor of 6 relative to air.

The cell is made large not only to accommodate large samples, but also to minimise the effect of reflected and scattered light from the sample on the cell walls. The cell may be made from H-30 Aluminum. When mechanically polished, this metal becomes highly reflective. Spectrosil WF (quartz) windows, with a thickness of 0.2 mm, have been used as they possess transmittance in excess of 99% for all incident light in the photon range 0.42 eV to 6.2 eV. Sealing means such as rubber O-rings and or neoprene cushions may be provided to ensure a good acoustic seal from the ambient surroundings.

The microphone used to detect the photoacoustic signal may be a single FG3329 electret microphone manufactured by Knowles Electronics. This miniature cylindrical device, of dimension 2.59 mm in diameter and 3.22 mm in length, is housed in an antechamber under the sample stage. This ensures that no scattered light induces noise from the microphone diaphragm. Only one microphone is used according to this embodiment of the invention, although it will be appreciated that cell can be easily modified accommodate a detector array. The microphone possesses a nominally high flat sensitivity of 2.5 mV/Pa in the frequency range 100 Hz to 10 kHz making the microphone ideal for studies at different chopping frequencies. In the case of a detector array the signal to noise ratio scales with the square root of the number of microphones.

Short Arc Xenon Lamp

According to the present invention a polychromatic light source is used to provide the incident light. An example of such a light source is a 300 W xenon short arc lamp as manufactured by LOT Oriel, with an arc size of 0.7 mm-2.4 mm, primary condensing optics, secondary coupling optics and with a high voltage power supply to provide the radiation source. A parabolic reflector is situated behind the lamp to enhance device efficiency. As the arc lamp is at the focal point of the primary condensing lens, this lens provides a collimated beam for the secondary lens, which in turn performs the number matching with the monochromator situated at its focal point, thus maximising throughput. The lamp provides reasonable constant irradiance from 250 nm to 2400 nm. The lamp is ozone free and consequently suffers from strong attenuation below 250 nm (above 4.96 eV).

In comparison to other non-ozone free lamps of similar output, the constant irradiance above the oxygen cut-on wavelength makes the lamp quite suitable for photoacoustic spectroscopy.

Optical Chopper

A variable frequency enclosed optical chopper manufactured by LOT Oriel is inserted in the path of the collimated beam between the primary and secondary condensing lenses. Hence, the collimated light is intensity modulated before being focused on the entrance slit of the monochromator. An ancillary benefit of the enclosure is the minimisation of acoustic noise arising from the air being chopped. The enclosure surrounding the wheel also aids in safeguarding the user against hazardous scattered light from the arc lamp. The chopping frequency may be varied from sub-Hz to 3 kHz by selection of an appropriate chopping wheel. In an exemplary embodiment, the system is configured to operate at a maximum modulation frequency of 350 Hz. The maximum modulation frequency depends on the chopper used. It will be noted that as chopping frequency increases the output signal decreases, and at very high chopping frequency (about 1 kHz) thermo-viscous damping occurs, which is undesirable in the application of the present invention. To avoid effects of thermally reflected waves and thermo-viscous damping, the usable chopping frequency range is typically of the order of about 10 Hz to about 1 kHz.

The device may operate in stand-alone mode or from a supplied external reference. In the exemplary system configuration described herein, the reference signal for the optical chopper is supplied by an internal signal generator in the lock-in amplifier. The reason for this is twofold: firstly, it ensures that the detection frequency and excitation frequency are identical with a zero phase difference between them, and secondly, as the frequency generated by the lock-in amplifier is fully programmable this enables control software to be written where the modulation frequency can be varied at the users discretion, by setting a desired modulation frequency value.

High Resolution Monochromator

An example of a monochromator that is suitable for use in the arrangement of the present invention is the Cornerstone 260 monochromator manufactured by LOT Oriel. It has entrance and exit focal lengths of 260 mm, a potential spectral operating range of 180 nm to 20 μm depending on the diffraction gratings used. The afore-mentioned limitations of the Xenon arc lamp that are imposed by ozone attenuation below 250 nm (above 4.96 eV) may be overcome by purging the instrument with nitrogen. Thus, through nitrogen purging, it is possible to extend the use of the Xenon arc lamp in the analysis of semiconductor materials to those having bandgaps greater than about 4.6 eV and as such all materials in the range 0.5 eV to 6.2 eV.

The device has a motorised triple grating turret, which facilitates rapid broad-spectrum scans at a maximum scan rate of 175 nm/s.

If monochromatic light strikes a grating, then a fraction of the light is diffracted into each order in accordance with the grating equation, as will be well known by those skilled in the art. The fraction diffracted into any order can be termed the efficiency of the grating in that order. Gratings are not equally efficient at all wavelengths for numerous reasons as the efficiency can be tuned by changing the number of grooves (or lines) in the grating, the groove facet angles and the shape or depth of the grating lines. The optimisation of efficiency by appropriate groove shaping is known as blazing. The blaze wavelength is the wavelength for which the grating is most efficient. Generally two types of grating are used: holographic and ruled. Holographic gratings provide good spectral resolution at the expense of reduced intensity, whilst ruled gratings offer increased intensity over the spectral range of interest at the expense of spectral resolution. The resolution of a grating increases and the throughput decreases with the number of grating lines. With these technical points and knowledge of the arc lamp spectrum in mind the following gratings were used in the monochromator, although it will be appreciated that different configurations may require alternative parameters.

TABLE 2.1

Gratings used in monochromator.

| Grating No. | Type | No. of Grooves (l/mm) | λ range (nm) | Blaze λ(nm) |
|---|---|---|---|---|
| 1 | Holographic | 1200 | 180-650 | 250 |
| 2 | Ruled | 1200 | 450-1400 | 750 |
| 3 | Ruled | 600 | 900-2800 | 1600 |

The performance of a monochromator may be evaluated in terms of its resolution, accuracy, precision and dispersion. The bandpass is the spectral width of radiation passed by a monochromator when illuminated by a light source with a continuous spectrum. By reducing the width of the input and output slits of the monochromator, the bandpass may also be reduced until a limiting bandpass is reached. The limiting bandpass is termed the resolution of the device. In spectral analysis, the resolution is a measure of the ability of the instrument to separate two spectral lines that are close together. The resolution of the Cornerstone 260 is 0.15 nm for a 1200 1/mm grating when used with entrance and exit slits with dimension 10 μm×2 mm. By judicious variation of the input and output slit widths, a relatively constant bandpass can be obtained for the entire wavelength range of a photoacoustic spectral scan. Attached to the monochromator input and output ports are continuously variable micrometer driven slits whose width may be varied from 4 μm to 3 mm and their height from 2 mm to 15 mm.

The monochromator has an accuracy of 0.35 nm and will reproduce wavelengths to a precision of 0.08 nm. It has an efficiency above 80% for blaze wavelengths and exhibits high dispersion, typically 0.31 mm/nm and 0.16 mm/nm for the wavelength ranges 180 nm to 1400 nm and 900 to 2800 nm, respectively.

Coupled to the output slit of the monochromator is a six-position filter wheel. For the spectral range of interest, three filters are necessary to remove the effect of higher order harmonic contamination in the output spectrum. The filters and the associated grating wavelength ranges that they operate for are presented in Table 2.2. These order sorting filters will also minimise the effect of stray re-entrant light in the monochromator. In a system with the potential to scan such a large range of wavelengths, this component becomes an integral part of the system. The filter change mechanism is controlled directly by the monochromator, which itself may be controlled using a dedicated hand controller, the IEEE 488.2 GPIB or the RS-232 communication protocols.

TABLE 2.2

Filters used with monochromator.

| Filter No. | Cut-on wavelength (nm) | Grating No. | λ range (nm) |
|---|---|---|---|
| 2 | 324 | 1 | 340-650 |
| 4 | 830 | 2 | 850-1200 |
| 6 | 1600 | 3 | 1750-2400 |

It will be appreciated that the degree of spectral resolution achievable using hand driven slits is not as high as what may be provided by computer controlled slits. It will therefore be appreciated that if good spectral resolution is desired that a utilisation of such computer controlled motor driven slits enable one to vary the slit width according to the spectral position of interest and thereby achieve a constant spectral bandpass over the energy range of interest.

Electrical Hardware

It will be understood that by using a lock in amplifier in combination with a data acquiring system that it is possible to acquire data from the lock-in amplifiers whilst simultaneously controlling the monochromator It is possible to single out the component of a signal at a specific reference frequency and phase. An important part of this process is that noise signals at frequencies other than the reference frequency are rejected. Hence, they do not affect the measurement.

An example of a lock-in amplifier which may be used in the photoacoustic spectrometer of the present invention is the Stanford Research Systems SR830 digital signal processing amplifier. The amplifier converts the amplified experimental signal using a 16 bit ADC that has a sampling frequency of 256 kHz. An anti-aliasing filter prevents higher frequency inputs from aliasing below 102 kHz. Using the digital PSD's linear multipliers, the digitised experimental signal is multiplied with the digitally computed reference signal. The reference sine wave may be considered "pure" as all harmonics are attenuated with a dynamic reserve of 100 dB. The lock-in amplifier has time constants from 10 μs to 30 ks with 6 dB to 24 dB per octave filter rolloff. The internally generated reference signal is accurate to within 25 ppm and phase measurements can be made with a resolution of 0.01°. The amplifier provides dual inputs and outputs in conjunction with an output reference port. Inputs can be supplied in differential or single ended mode. The two data displays can be used for the display of X and Y or R and θ. The digital lock-in is better than it analogue counterpart as it does not suffer from drift in the PSD's.

Low-Noise Preamplifier

To further enhance the electrical signal generated by the microphone, the use of a Stan-ford Research Systems SR552 low-noise bipolar input voltage preamplifier may be employed. The preamplifier is designed to supply gain to the experimental detector, before the signal to noise ratio is permanently degraded by cable capacitance and noise pick-up. The amplifier has an input impedance of 100 kOhm+25 pF and a common mode rejection ratio of 110 dB at 100 Hz. Signals can be supplied in differential or single-ended mode. It has a full-scale sensitivity from 10 nV to 200 mV. Thus the preamplifier minimises noise and reduces measurement time in noise limited experiments. The power and control signals for the device are supplied directly by the SR830 lock-in amplifier.

When used in conjunction with the lock-in amplifier, the gain is set to 10. It is therefore necessary to divide all output measurements by 10 to obtain the true measurement value.

Electrical Connections

Due to the small size of the microphone and its positioning within the photoacoustic cell, attachment of coaxial cables to the signal lines was not possible. Therefore, small insulated wires from the microphone were connected inside a Gaussian shield to a twisted coaxial network that was fed to the input preamplifier in a differential mode configuration. The output from the preamplifier was also fed to the lock-in amplifier through twisted pair coaxial cables in a differential mode configuration. The microphone requires a supply voltage of 0.9 V to 1.6 V volts and this was supplied from a standard laboratory power supply. All of the electronic circuitry i.e. the microphone and its power supply, the lock-in amplifier, the optical chopper driver and the monochromator were all powered from a mains voltage supply independent to that supplying the arc lamp power supply. This ensured any potential voltage variations due to the operation of the lamp did not couple into the rest of the system. A plurality of switchable microphones may also be used to enhance the photoacoustic signal-to-noise ratio.

Control Hardware

The full potential of the optical and electrical equipment previously described can only be harnessed by placing the entire system under the control of a personal computer. All the equipment in the system may be controlled directly or indirectly via the IEEE 488.2 GPIB or RS-232 communication standards. Conventional GPIB provides a modular robust approach for interfacing up to fifteen devices on a single data bus. Unlike RS-232, where parameters such as baud rate, parity and the number of stop bits have to be known, any device adhering to the GPIB standard may be connected to the bus with little or no knowledge of its communication requirements. In conjunction, RS-232 does not readily permit simultaneous communication with several devices without the use of sophisticated hardware or software routines.

GPIB devices communicate with each other by sending device-dependent messages and interface messages through the interface system. Device-dependent messages, commonly known as data messages, contain device specific information such as programming instructions that control its operation. Interface messages are primarily concerned with bus management. Interface messages perform functions such as initialising the bus and addressing devices. GPIB devices may be categorised as talkers, listeners and controllers. Listeners are devices that may receive data transmitted by a talker. For example, in the spectrometer, the lock-in amplifier acts as both a talker (transmitting data to the computer) and a listener (acquiring data from the microphone via the preamplifier). The controller, a PCI card in this application, manages the flow of information on the bus by sending commands to all the devices.

Devices are usually connected via a shielded 24-conductor cable with both a plug and receptacle connector at each end. The bus uses negative logic with standard TTL levels. In order to achieve the high data transmission rates, nominally 1.5 Mbytes/s when using a PCI controller, the physical distance between devices is limited as follows. The maximum separation between any two devices should be less than 4 m and the average device separation must not be greater than 2 m over the entire bus. The total cable length must not exceed 20 m.

Software

The software developed for the photoacoustic spectrometer essentially falls into two functional categories, that of data acquisition and data processing. The data acquisition software is responsible for the communication and control of all the experimental apparatus. Due to the low signal to noise ratio inherent in photoacoustic spectroscopy, once spectra have been recorded they normally have to undergo processing of some sort before they can be interpreted correctly.

Data Acquisition Software

An ancillary benefit of the IEEE 488.2 GPIB standard is that several companies have developed sophisticated high-level application development tools to enable engineers to provide application specific user interfaces to their GPIB fostered systems. Lab-View, a product of National Instruments Inc., is a graphical program development environment. Lab View programs are called virtual instruments, or VIs for short, because their appearance and operation mimic the actual operation of the device they communicate with. A VI consists of an interactive user interface, a data-flow diagram that serves as the source code and icon connections that allow the VI to be called from higher level VIs. When amalgamated with Lab View GPIB compliant instrument drivers, sophisticated control systems may be developed with little time overhead. Several VIs or alternative software code may be used to control both the monochromator and the lock-in amplifier.

Photoacoustic Energy Scan

The present invention provides a photoacoustic spectrometer for the characterisation of sub-bandgap absorption defects. The method is typically effected using a plurality of method steps such as:

a) providing a light source having a polychromatic output substantially in the photonic energy range 0.5 eV to 6.2 eV, b) setting the wavelength of the light source to an initial first irradiating wavelength, c) irradiating the sample with said light source and detecting the acoustic signal emitted by the sample at said wavelength, d) incrementing the wavelength by a sequence of increment values so as to provide a plurality of irradiating wavelengths and detecting the acoustic signal emitted by the sample at each of said irradiating wavelengths, and e) relating each of the detected acoustic signals to the incident wavelength effecting generation of said acoustic signal.

It will be appreciated that such methodology may be effected using a plurality of different techniques. One example of a typical VI that may be used for such studies will be examined with reference to the flowchart for the photoacoustic energy scan VI illustrated in FIG. 5. It will be appreciated that the parameters utilised in this exemplary embodiment are typical of values that may be used and are not intended to limit the present invention to such values. Prior to starting the VI, the user enters the start wavelength, end wavelength and wavelength increment for the scan. The user specifies the number of scans that are to be performed and also provides the details of where the data is to be stored. The VI is then started and proceeds according to the flowchart and to the following steps:

Step 1: Moving to the initial wavelength,

Step 2: Pausing for 2 s,

Step 3: Increasing wavelength by a user-selectable increment,

Step 4: Pausing for 5 t, where t is the time constant for a lock-in input filter, Step 5: Reading and displaying the current wavelength, Step 6: Reading the photoacoustic signal magnitude from the lock-in amplifier, Step 7: Reading the photoacoustic signal phase from the lock-in amplifier, Step 8: Repeating Steps 3 to 7 until the current wavelength equals the final wavelength, Step 9: Writing data to file, Step 10: Repeating Steps 1 to 9 in accordance with the number of scans preset by the user.

Step 11: Finish.

Data Processing Software

In a normal photoacoustic energy scan, the data is collected from a number of different spectra. Since the noise is assumed to be Gaussian in nature simple statistically averaging should improve the signal to noise ratio. The averaged spectrum is next normalised to an averaged spectrum of a known sample such as carbon black powder. As averaging cannot remove all of the spectral noise, some filtering is necessary at this stage. All of these processes will now be examined.

Spectral Averaging

During a photoacoustic energy scan, the signal magnitude and phase are read from the lock-in amplifier as the wavelength of the incident light is varied. These three elements are recorded in an ASCII text file. For a spectrum from a carbon black powder where the photoacoustic effect is quite strong, nominally five scans across the wavelength range of interest are recorded. For a semiconductor sample it is necessary to record twenty or more scans to minimise the effect of noise. Having recorded the spectra, they are statistically averaged. A C program has been written that reads the directory where the spectra are stored, loads them into memory and takes the simple average. The average is then stored in a separate file for normalisation.

Spectral Normalisation

When a photoacoustic spectrum is recorded, superimposed on the signal from the sample itself is a photoacoustic signal due to the spectral distribution of the optical system, the cell and the microphone. Normalisation is the process where these errors are corrected.

This is performed by normalising the photoacoustic response of the specimen with that of a fine powder of carbon black. The latter acts as a true light trap with flat response at all wavelengths. During the normalisation procedure the user is asked to enter the name of the averaged spectrum to be normalised along with the name of the averaged carbon black spectrum used in the process. Each sample spectral point is divided by its corresponding carbon black point. The normalised data is then stored in a file for filtering.

Spectral Filtering

Due to the fact that the constructed spectrometer is a single beam one, and therefore, by the process of normalisation fluctuations in the normalised photoacoustic spectrum are bound to happen. The previous averaging and normalisation processes in themselves could enter some element of noise which could alter to some extent the final result. It is therefore desirable to perform some form of spectral filtering or smoothing to remove any noise. Two filters have been developed for use with the data. The first is a simple n-point smoothing window where each spectral point is replaced by a local average of the $n_L$ data points to the left and $n_R$ data points to right of it. The user specifies the number of points to be averaged. In general, it is not recommended to average more than five points at a time or the spectrum may be corrupted. Mathematically the form of this filter may be expressed as follows:

$$g_i = \sum_{n=-n_L}^{n_R} C_n f_{i+n} \tag{8}$$

where $g_i$ is the filtered value for the spectral point $f_i$. The coefficient $c_n = 1/(n_L + (n_L+1))$. It will be appreciated that such a moving average filter works quite well for carbon black powders as their signal to noise ratio is quite high. However, for spectra from semiconductor samples it is dangerous to use such a filter. Suppose the spectrum could be approximated by a function that is sufficiently differentiable such that its second order derivative exists. In such cases, the moving average filter has the mathematical property of reducing the value of the function when a local maximum occurs. In a spectroscopy application, this implies a narrow spectral line will have its height reduced and its width increased. Since these parameters are themselves of physical interest, such filtering is obviously erroneous. Note however, that a moving average filter will preserve the area under the peak of interest i.e. the zeroth moment.

For spectroscopy applications a filter is required that preserves the zeroth and higher order moments. One such filter that may be implemented is the Savitzky-Golay filter. This type of filter has the advantage that it operates directly in the time-domain, and therefore, data does not have to be transferred back and forth between the Fourier domain. This avoids the risk of any loss of information, i.e. introduction of noise, due to algorithms such as the fast Fourier transform that might be used for such a process. The basic idea behind the Savitzky-Golay filter is to find filter coefficients $c_n$ that preserve higher order moments. Equivalently, the idea is to approximate the underlying function with a moving polynomial window. At each point $f_i$ a polynomial is least-squares fitted to all n points in the moving window, and then $g_i$ is set to be the value of that polynomial at position i.

Photoacoustic Depth Profiling

The apparatus of the present invention may be adapted to provide for photoacoustic depth profiling. It will be appreciated that as the probe depth, i.e. the depth to which the thermal wave generated through pohotexcited carrier diffusion (the depth to which the incident beam is irradiated) penetrates into the sample, is adjusted by varying the chopping frequency, it may be possible to carry out depth profiling on the sample. The relationship between the thermal diffusion length of the heat source (the probe depth) generated by the exciting light source and the radial frequency of the chopping/modulation of the light source is shown in the following equation:

$$a = (\omega/2\alpha)^{0.5} \qquad (9)$$

wherein a is the thermal diffusion coefficient, $\omega$ is the chopping frequency, and a is the thermal diffusivity, and where $$\alpha = k/\rho C \qquad (10)$$

wherein k is the thermal conductivity, $\rho$ is density and C is the specific heat.

As shown in FIG. 1, the PC can control the optical chopper via the lock-in amplifier. Thus, by varying the modulation frequency through a judicious selection of a suitable optical chopper, it is possible to probe information from different thermal lengths within a sample.

For example, with a sample of Si, at 50 Hz and 300 Hz the probe depths are 742 micrometers and 302 micrometers. This is in contrast to the penetration depth of the incident optical photons—suppose they have energy approx. 1.3 eV then their penetration depth is about 100 micrometers. Therefore PAS can obtain information from regions (i.e. probe depths) not conventionally accessible through optical techniques such as photoluminescence and Raman spectroscopy (both of which incidentally are radiative techniques). Thus one could envisage probing dopant distributions in wafers as a function of depth and position on the wafer and building up a 3-D tomographic image of same. This may be used, for example, in the study of the thermoelastic properties of semiconductor materials in particular at dopant interfaces.

It will be appreciated that means may be provided for cooling or heating the cell to allow the effect of temperature on the photoaccoustic signal to be monitored. The means for cooling may be adapted to maintain the cell at temperatures in a controllable range from below 273K. For temperatures down to about 77K, apparatus such as a cryostat (for temperatures down to 77K) or Peltier cooler (for 215K -273K range) may be used. Alternatively, liquid helium may be used to cool the sample further, at which temperature the non-radiative or phonon mediated effects should disappear or be significantly reduced. In one embodiment, the cell may be adapted so as to allow liquid helium to pass through the walls of the cell to cool the sample indirectly. It will be appreciated that in accordance with the classical photoacoustic theory of Rosencwaig and Gersho that this cooling will serve to improve the photoacoustic signal-to-noise ratio Again, when heating the cell, the means for heating may heat the sample directly or indirectly. For example, the cell may include a heating stage which may be used to control the temperature of the cell over a specific range. It will be appreciated that the sample may be heated directly by applying an electric field across the sample material in a direction perpendicular to the direction of the incident light, thus encouraging Joule heating of the sample.

It will be further appreciated that it may therefore be possible to record the acoustic signal over a range of sample temperatures, so as to enable the relationship between temperature and the acoustic signal to be investigated. Software may be provided to enable a photoacoustic spectra to be recorded during heating or cooling of the sample. The effect of change of temperature on the stress of the sample may then be investigated.

Figure 6:
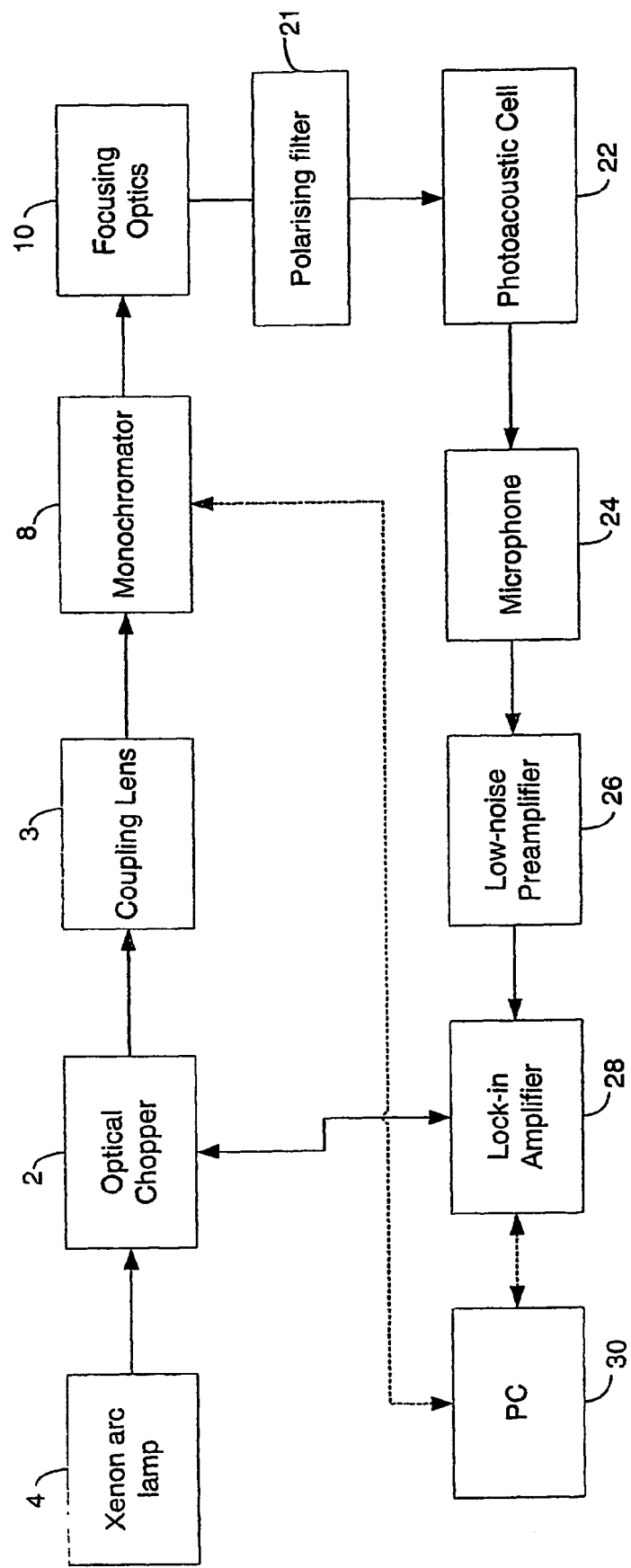
FIG. 6 is a schematic representation of a photoacoustic spectrometer according to a second aspect of the present invention.

The invention further provides apparatus and a method for measuring dielectric anisotropies within a dielectric sample. FIG. 6 shows a photoacoustic spectroscopy apparatus incorporating a polarising filter to polarise the incident light beam. The apparatus comprises the same features as that in FIG. 1, the only addition being the polarising filter 21.

The polarising filter 21 is provided in the optical path or train just prior to the light entering the photoacoustic cell. Rotation means are further provided to rotate the polarising filter 21 in a plane perpendicular to the direction of the light beam. Rotating the filter has the effect of adjusting the polarisation of the photons impinging on the sample under test. The rotation means are automatically controlled, by typical automated means such as an automated motor. It will be appreciated that the rotation of the filter may alternatively be manually controlled.

The polarisation filter is a standard polarisation filter. The rotation means comprises a rotation mount or stage on which the polarisation filter sits.

Figure 7:
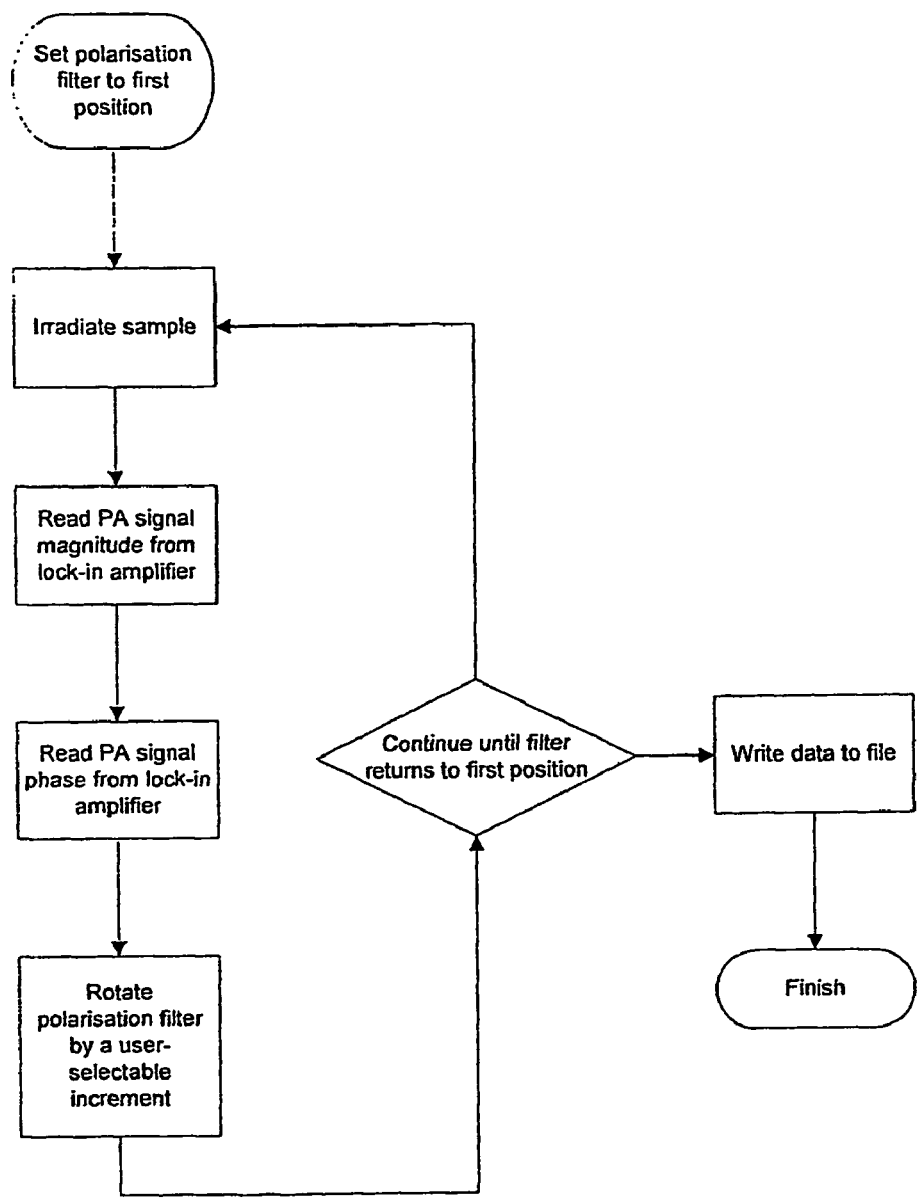
FIG. 7 is a flow chart showing sequence steps that may be undertaken, in accordance with the present invention, so as to provide a spatial scan of dielectric anisotropy.

Using this apparatus, it is possible to carry out investigations into the nature of anisotropies in the dielectric sample. A method of recording photoacoustic response as a function of polarisation is shown in FIG. 7. The method may be used to yield direct information on the nature of dielectric anisotropy.

Dielectric Anisotropy Spatial Scan

The method is typically effected using a plurality of method steps such as:
 a) providing a light source having a polychromatic output substantially in the photonic energy range 0.5 eV to 6.2 eV,
 b) setting the polarising filter to a first position,
 c) irradiating the sample with said polarised light source and detecting the acoustic signal emitted by the sample at said polarity, d) rotating the polarising filter by a sequence of increment values so as to incrementally vary the polarisation of the incident light on the sample and detecting the acoustic signal emitted by the sample at each of said irradiating polarity, and e) relating each of the detected acoustic signals to the polarity of the incident light effecting generation of said acoustic signal.

It will be appreciated that such methodology may be effected using a plurality of different techniques. One example of a typical scan method that may be used for such studies will be examined with reference to the flowchart for the photoacoustic energy scan illustrated in FIG. 7. It will be appreciated that the parameters utilised in this embodiment are typical of values that may be used and are not intended to limit the present invention to such values.

Prior to starting the scan, the user specifies the number of scans that are to be performed and also provides the details of where the data is to be stored. The scan is then started and proceeds according to the flowchart and to the following steps:

Step 1: Rotating the polarisation filter to the start position,
Step 2: Reading the photoacoustic signal magnitude from the lock-in amplifier,
Step 3: Reading the photoacoustic signal phase from the lock-in amplifier,
Step 4: Rotating filter by a user-selectable increment,
Step 5: Repeating Steps 2 to 4 until the filter is fully rotated back to the start position
Step 6: Writing data to file,
Step 7: Repeating Steps 1 to 6 in accordance with the number of scans preset by the user.
Step 8: Finish.

Figure 5:
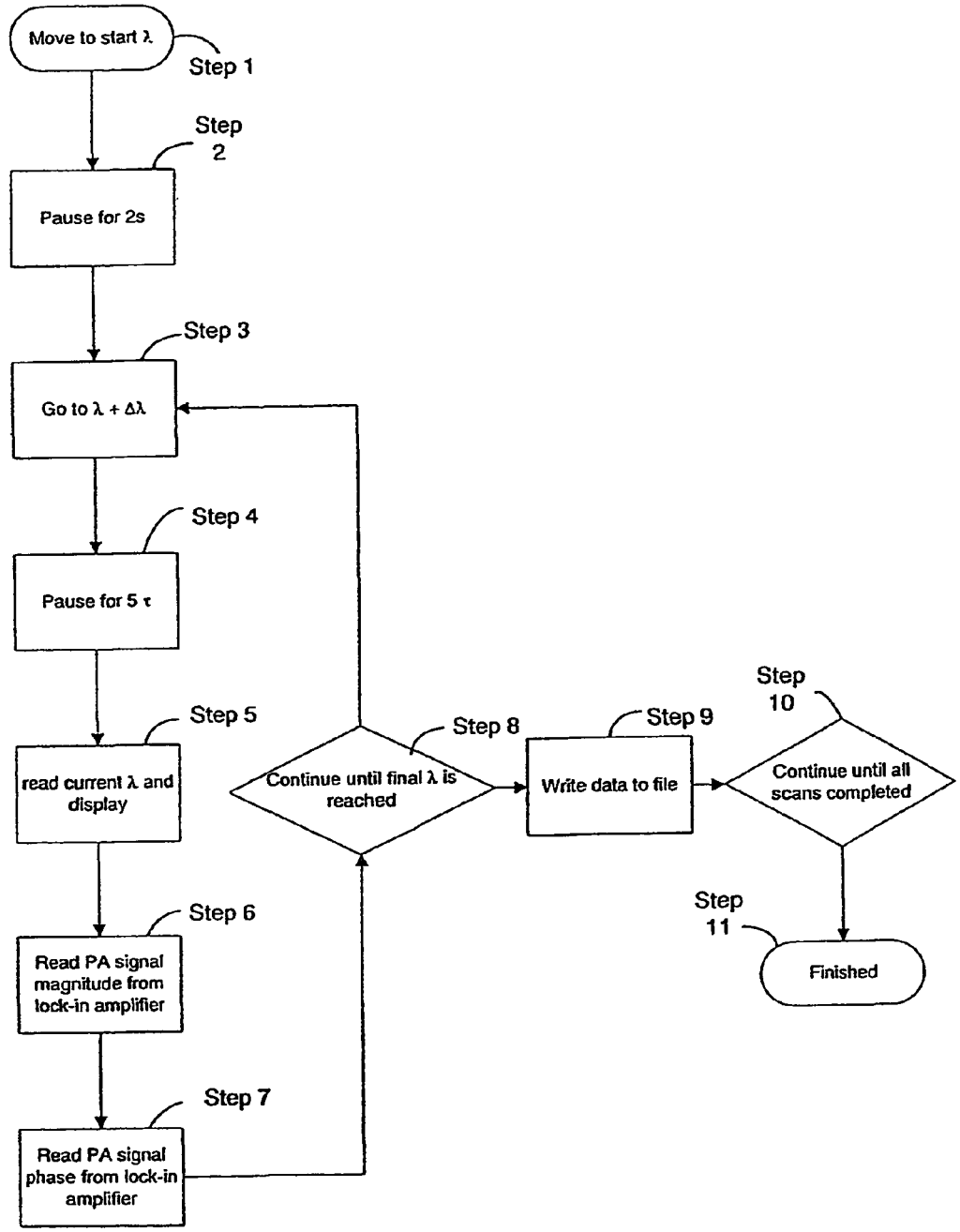
FIG. 5 is a flow chart showing sequence steps that may be undertaken, in accordance with the present invention, so as to provide a photoacoustic energy scan of a sample material.

It will be appreciated that the above method may further comprise the step of varying the wavelength of the light for each scan, as previously described with reference to FIG. 5.

It will be understood that herein has been described a method and apparatus for investigating the photoacoustic spectrum of sample materials in an extended wavelength range to that hereinbefore possible. In preferred embodiments, the range is over the entire spectrum of about 0.5 eV to about 6.2 eV, although it will be appreciated that for certain materials sub-ranges within this extended range may be determined as being more suitable and as such the obtaining of data from a complete spectrum will not be required. It will be further appreciated that the methodology and system of the present invention enable an investigation of distinct areas within a sample material such that specific defects may be associated with specific areas on the sample material and that other areas may be defined as being substantially defect free. Such spatial analysis of a sample material provides a more efficient analysis of a sample material than hereinbefore possible.

The words "comprises/comprising" and the words "having/including" when used herein with reference to the present invention are used to specify the presence of stated features, integers, steps or components but does not preclude the presence or addition of one or more other features, integers, steps, components or groups thereof.

The invention claimed is:

1. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:

a) a light source having a polychromatic output substantially in the photonic energy range 0.5 eV to 6.2 eV,
b) focusing apparatus adapted to couple the output from the light source onto the sample material, the focusing apparatus providing for an alignment and focusing of the light emitted from the light source so as to provide a substantially parallel incident light onto the sample material,
wherein the focusing apparatus comprises:
a 1st optical focusing system having a two lens arrangement, adapted to provide for a maximisation of the photonic throughput thereby maximising the intensity of light incident on the sample, and wherein the first and second lenses are provided by a biconcave and biconvex lens respectively; and
a 2nd optical focusing system being adapted to provide for an increment in the spatial resolution of the light from the light source; and
c) a detector for detecting and acquiring said acoustic signal emitted by the sample in response to said irradiation.

2. The apparatus as claimed in claim 1 further including a modulator for modulating the polychromatic light.

3. The apparatus as claimed in claim 2, wherein the modulator includes an optical chopper.

4. The apparatus of claim 2 additionally including a monochromator provided between the light source and the focusing means, the monochromator adapted to convert the modulated polychromatic light into modulated monochromatic light.

5. The apparatus as claimed in claim 4 wherein the monochromator comprises means for altering the output slit width to optimise one or more of incident power, spectral and spatial resolution, PA signal-to-noise ratios.

6. The apparatus as claimed in claim 4 further including means to vary the input slit to the monochromator.

7. The apparatus of claim 1 wherein the detector includes a plurality of microphones provided within the photoacoustic cell, the microphones being adapted to detect an acoustic emission from the sample upon radiation by the light source.

8. The apparatus as claimed in claim 7 wherein the microphones are of the type known as electret microphones.

9. The apparatus of claim 1 wherein said detector detects and acquires a signal associated with a sub-range defined within the photonic energy range output of the light source.

10. The apparatus of claim 1 wherein said detector includes a data processor and a signal processor.

11. The apparatus of claim 1 being further adapted to enable a recordal of numerous spectra.

12. The apparatus of claim 1 wherein said detector includes:
a) a pre-amplifier for pre-amplifying an electrical signal, such as a low-noise pre-amplifier, and
b) a lock-in amplifier.

13. The apparatus as claimed in claim 12 wherein a detected signal is passed through a low-noise pre-amplifier to a lock-in amplifier, and the amplified signal is then passed to a computer.

14. The apparatus of claim 1 wherein the photoacoustic cell is provided with an inert atmosphere such as helium gas.

15. The apparatus of claim 1 additionally including a cooler for cooling the cell to below 273K.

16. The apparatus of claim 15, wherein the cooler is adapted to maintain the cell at temperatures in a controllable range from about 77K to about room temperature by means of apparatus such as a cryostat or Peltier cooler.

17. The apparatus of claim 1 additionally including a heater for heating the cell.

18. The apparatus of claim 17, wherein the heater is adapted to apply an electric field across the sample material in a direction perpendicular to the direction of the incident light, to encourage Joule heating of the sample.

19. The apparatus of claim 15, further comprising a recorder for recording the acoustic signal over a range of temperatures, so as to enable the relationship between temperature and the acoustic signal to be investigated.

20. The apparatus of claim 1 wherein the focusing apparatus is adapted to provide an incident light beam having dimensions not greater than about 15 mm in diameter, the diameter of the incident light being substantially equivalent to the spatial resolution achievable.

21. The apparatus as claimed in claim 1 wherein the first optical system is adapted to provide for a magnification factor of the image of less than 1 and preferably about 0.3.

22. The apparatus as claimed in claim 1 wherein the first lens is configured to provide a virtual image as the source image which then provides a real image as the incident light on the sample.

23. The apparatus as claimed in claim 1 wherein the 2nd optical focusing signal is adapted to provide for spatial mapping of the photoacoustic signal produced at the cell.

24. The apparatus as claimed in claim 23 adapted to allow relative movement between the beam and the sample to enable different portions of the sample to be analysed.

25. The apparatus as claimed in claim 24 wherein the photoacoustic cell is mountable on a computer controlled X-Y translational stage so as to enable a movement of the cell relative to the incident light, such relative movement enabling the formation of a spatially resolved map of the photoacoustic signal to be computed.

26. The apparatus as claimed in claim 1 wherein the second optical system comprises a plurality of optical components which are adapted to re-configure the spatial dimensions of the light emitted from the monochromator so as to form an incident light beam.

27. The apparatus as claimed in claim 26 wherein the second optical system includes:
   a) a cylindrical lens adapted to re-configure the dimensions of the light incident thereon, the cylindrical lens providing a light beam substantially circular in cross section as an output thereof,
   b) a concave mirror adapted to re-direct and focus the substantially circular light onto a 1st plane mirror which is adapted to further re-direct the light beam so as to provide a source image for the first optical system, and
   c) a 2nd plane mirror adapted to receive the magnified output from the first optical system and re-direct that light onto the sample within the photoacoustic cell.

28. The apparatus as claimed in claim 27 wherein the combination of the lens and mirror assembly provided by the first and second systems desirably delivers a circular shaped beam incident on the sample with a diameter variable between 1 mm and 12 mm.

29. The apparatus as claimed in claim 27 wherein the combination of a concave mirror and a cylindrical lens generates an image on the 1st plane mirror substantially equal in size in both horizontal and vertical directions.

30. The apparatus of claim 1 being further adapted to provide for a fully automated spatial resolved photoacoustic scan of a sample material.

31. The apparatus of claim 1, further comprising a chopping frequency adjustor for varying the chopping frequency of the incident beam so as to enable the penetration depth of the beam into the sample to be controlled, such depth controlling enabling depth profiling of the sample to be investigated.

32. The apparatus of claim 1 further comprising a polarising filter located between the focusing apparatus and the photoacoustic cell, the polarising filter adapted to polarise the incident light beam.

33. The apparatus of claim 32 wherein the polarising filter comprises an adjustor for adjusting the direction of the polarisation of the incident light beam.

34. The apparatus of claim 33, wherein the adjustor is adapted to rotate the polarising filter in a plane perpendicular to the direction of the incident light beam.

35. The apparatus of claim 34, wherein the adjustor for rotating the polarising filter is automatically controlled.

36. A method of providing an acoustic signal spectrum emitted by a sample material provided within a photoacoustic cell following irradiation of the sample by an incident light beam, the method comprising the steps of:
   a) providing a light source having a polychromatic output with a photonic energy range of 0.5 eV to 6.2 eV,
   b) providing a $1^{st}$ optical focusing system having a two lens arrangement, adapted to provide for a maximization of the photonic throughput thereby maximizing the intensity of light incident on the sample, and wherein the first and second lenses are provided by a biconcave and biconvex lens respectively;
   c) providing a 2nd optical focusing system being adapted to provide for an increment in the spatial resolution of the light from the light source;
   d) setting the wavelength of the light source to an initial first irradiating wavelength,
   e) irradiating the sample with said light source and detecting the acoustic signal emitted by the sample at said wavelength,
   f) incrementing the wavelength by a sequence of increment values so as to provide a plurality of irradiating wavelengths and detecting the acoustic signal emitted by the sample at each of said irradiating wavelengths, and
   g) relating each of the detected acoustic signals to the incident wavelength effecting generation of said acoustic signal.

37. The method as claimed in claim 36 wherein the signal detected at each of said wavelengths includes phase and magnitude information.

38. A method of providing an acoustic signal spectrum emitted by a sample material provided within a photoacoustic cell following irradiation of the sample by an incident light beam, the method comprising the steps of:
   a) providing a sample selected from one or more of the following:
      i) infrared detector materials such as InAs,
      ii) wide bandgap semiconductors for blue/violet/UV light emissions,
      iii) high temperature electronics (e.g. GaN, SiCor diamond), and
      iv) SI or GaAs based materials,
   b) providing a light source having a output with a photonic energy range of 0.5 eV to 6.2 eV,
   c) polarising the incident light beam from the light source,
   d) irradiating the sample with said polarised light beam and detecting the acoustic signal emitted by the sample,
   e) adjusting the direction of polarisation so as to provide polarisation in a plurality of directions and detecting the acoustic signal emitted by the sample at each direction of polarisation, and f) relating each of the detected acoustic signals to the polarization direction of the incident light effecting generation of said acoustic signal.

39. The method as claimed in claim 38, wherein the step of polarising the incident light beam comprises the step of positioning a polarising filter in the path of the incident light beam.

40. The method as claimed in claim 38, wherein the step of adjusting the direction of polarisation comprises the step of rotating the polarising filter in a plane perpendicular to the direction of the incident light beam.

41. The method of claim 38 wherein the signal detected includes phase and magnitude information.

42. The method of claim 38 further comprising the step of converting the polychromatic light into a modulated monochromatic light prior to irradiation of the sample.

43. The method of claim 38 further comprising the step of effecting relative movement between a light beam emitted from the light source and incident on the sample and the sample to enable different portions of the sample to be analysed.

44. A method of providing an acoustic signal spectrum emitted by a sample material provided within a photoacoustic cell following irradiation of the sample by an incident light beam, the method comprising the steps of:
  a) providing a sample selected from one or more of the following:
    i) infrared detector materials such as InAs,
    ii) wide bandgap semiconductors for blue/violet/UV light emissions,
    iii) high temperature electronics (e.g. GaN, SiC or diamond), and Si or GaAs based materials,
  b) providing a light source having an output substantially in the photonic energy range 0.5 eV to 6.2 eV,
  c) polarising the incident light beam from the light source,
  d) irradiating the sample with said polarised light beam and detecting the acoustic signal emitted by the sample,
  e) adjusting the direction of polarisation so as to provide polarisation in a plurality of directions and detecting the acoustic signal emitted by the sample at each direction of polarisation, and relating each of the detected acoustic signals to the polarization direction of the incident light effecting generation of said acoustic signal.

45. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:
  a) a light source having an output substantially in the photonic energy range 0.5 eV to 6.2 eV,
  b) focusing apparatus adapted to couple the output from the light source onto the sample material, the focusing apparatus providing for an alignment and focusing of the light emitted from the light source, and comprising a plurality of optical components which are adapted to re-configure the spatial dimensions of the light output from the light source so as to form an incident light beam,
  c) a detector for detecting and acquiring said acoustic signal emitted by the sample in response to said irradiation, and
  d) means for allowing relative movement between the incident light beam and the sample to enable different portions of the sample to be analysed so as to enable the formation of a spatially resolved map of the photoacoustic signal to be computed.

46. The apparatus as claimed in claim 45 being further adapted to provide for a fully automated spatial resolved photoacoustic scan of a sample material.

47. The apparatus as claimed in claim 45 wherein the means for allowing relative movement is a computer controlled X-Y translational stage on which the photoacoustic cell is mountable, so as to enable a movement of the cell relative to the incident light beam, such relative movement enabling the formation of a spatially resolved map of the photoacoustic signal to be computed.

48. The apparatus of claim 45 further comprising a polarising filter located between the focusing apparatus and the photoacoustic cell, the polarising filter adapted to polarise the incident light beam.

49. The apparatus of claim 48 wherein the polarising filter comprises an adjustor for adjusting the direction of the polarisation of the incident light beam.

50. The apparatus of claim 49, wherein the adjustor is adapted to rotate the polarising filter in a plane perpendicular to the direction of the incident light beam.

51. The apparatus of claim 50, wherein the adjustor for rotating the polarising filter is automatically controlled.

52. The apparatus as claimed in claim 45 further including means for modulating the light source's output.

53. The apparatus as claimed in claim 52, wherein the means for modulating includes an optical chopper.

54. The apparatus as claimed in claim 45 being further adapted to enable a recordal of numerous spectra.

55. The apparatus according to claim 45 wherein the light source comprises a laser.

56. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:
  a) a light source having an output substantially in the photonic energy range 0.5 eV to 6.2 eV,
  b) focusing apparatus adapted to couple the output from the light source onto the sample material, the focusing apparatus providing for an alignment and focusing of the light emitted from the light source so as to provide a substantially parallel incident light onto the sample material, and
  c) a detector for detecting and acquiring said acoustic signal emitted by the sample in response to said irradiation; and
  d) a heater for heating the cell adapted to apply an electric field across the sample material in a direction perpendicular to the direction of the incident light, to encourage Joule heating of the sample.

57. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:
  a) a light source having an output substantially in the photonic energy range 0.5 eV to 6.2 eV, b) focusing apparatus adapted to couple the output from the light source onto the sample material, the focusing apparatus providing for an alignment and focusing of the light emitted from the light source so as to provide a substantially parallel incident light onto the sample material, and c) a detector for detecting and acquiring said acoustic signal emitted by the sample in response to said irradiation; and d) a heater for heating the cell; and e) a recorder for recording the acoustic signal over a range of temperatures, so as to enable the relationship between temperature and the acoustic signal to be investigated.

58. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:

a) a light source having an output substantially in the photonic energy range 0.5 eV to 6.2 eV, b) focusing apparatus adapted to couple the output from the light source onto the sample material, the focusing apparatus providing for an alignment and focusing of the light emitted from the light source so as to provide a substantially parallel incident light onto the sample material, and c) a detector for detecting and acquiring said acoustic signal emitted by the sample in response to said irradiation; and d) a cooler adapted to maintain the cell at temperatures in a controllable range from about 77K to about room temperature.

59. The photoacoustic spectrometer apparatus of claim 58 wherein the cooler maintains the cell at temperatures in the controllable range from about 77K to about room temperature by means of apparatus such as a cryostat or Peltier cooler.

60. A photoacoustic spectrometer apparatus adapted to enable an observation and characterisation of non-radiative sub bandgap defects in narrow and large bandgap materials using photoacoustic spectroscopy techniques, the apparatus providing for an irradiation of a sample material provided within a photoacoustic cell and the subsequent detection and processing of an acoustic signal emitted by the sample, the apparatus comprising:

a) a light source having an output substantially in the photonic energy range 0.5 eV to 6.2 eV, b) focusing apparatus adapted to couple the output from the light source onto the sample material, the focusing apparatus providing for an alignment and focusing of the light emitted from the light source so as to provide a substantially parallel incident light onto the sample material, and c) a detector for detecting and acquiring said acoustic signal emitted by the sample in response to said irradiation;

d) a cooler for cooling the cell to below 273K; and e) a recorder for recording the acoustic signal over a range of temperatures, so as to enable the relationship between temperature and the acoustic signal to be investigated.

* * * * *

UNITED STATES PATENT AND TRADEMARK OFFICE
CERTIFICATE OF CORRECTION

PATENT NO.        : 7,586,611 B2                                     Page 1 of 1
APPLICATION NO.   : 10/557950
DATED             : September 8, 2009
INVENTOR(S)       : Lowney et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this

Fourteenth Day of September, 2010

David J. Kappos
*Director of the United States Patent and Trademark Office*